(12) United States Patent
Wong

(10) Patent No.: US 8,143,581 B2
(45) Date of Patent: Mar. 27, 2012

(54) ABSORPTION BIASED NDIR GAS SENSING METHODOLOGY

(76) Inventor: Jacob Y Wong, Goleta, CA (US)

( * ) Notice: Subject to any disclaimer, the term of this patent is extended or adjusted under 35 U.S.C. 154(b) by 0 days.

(21) Appl. No.: 12/859,749

(22) Filed: Aug. 19, 2010

(65) Prior Publication Data

US 2011/0042570 A1   Feb. 24, 2011

Related U.S. Application Data

(60) Provisional application No. 61/274,874, filed on Aug. 21, 2009.

(51) Int. Cl.
*G01N 21/61* (2006.01)

(52) U.S. Cl. ........................................ 250/345

(58) Field of Classification Search .................. 250/345
See application file for complete search history.

(56) References Cited

U.S. PATENT DOCUMENTS

| | | | |
|---|---|---|---|
| 3,793,525 A | 2/1974 | Burch et al. | |
| 3,811,776 A | 5/1974 | Blau, Jr. | |
| 5,026,992 A | 6/1991 | Wong | |
| 5,163,332 A | 11/1992 | Wong | |
| 5,222,389 A | 6/1993 | Wong | |
| 5,340,986 A | 8/1994 | Wong | |
| 5,341,214 A | 8/1994 | Wong | |
| 5,347,474 A | 9/1994 | Wong | |
| 5,502,308 A | 3/1996 | Wong | |
| 6,762,410 B1 * | 7/2004 | Wiechers et al. | 250/343 |
| 7,259,374 B2 | 8/2007 | Wong | |
| 7,358,489 B2 | 4/2008 | Wong | |
| 2008/0185524 A1 * | 8/2008 | Kanstad | 250/338.5 |

OTHER PUBLICATIONS

Jaffe,"Infrared measurement of Carbon Dioxide in the Human Breath":Breathe-Through Devices from Tyndall to the Present DayTechnology,Computing&Simulation 2008;107:#3 890-904.

* cited by examiner

*Primary Examiner* — Constantine Hannaher
(74) *Attorney, Agent, or Firm* — Wagner Anderson & Bright, P.C.; Roy L. Anderson

(57) ABSTRACT

An NDIR gas sensor and methodology use an absorption bias between signal and reference outputs to determine sample concentration of a gas being measured. The absorption bias is created by using a signal channel in a sample chamber with a signal path length that is greater than a reference path length of a reference channel in the sample chamber while both the signal and reference detectors have an identical narrow band pass filter with the same Center Wavelength ("CWL"), Full Width Half Maximum (FWHM) and transmittance efficiency at the CWL. Performance is improved when the reference detector and the signal detector share a common thermal platform that can also be shared by the sample chamber and the infrared source.

8 Claims, 5 Drawing Sheets

ABSORPTION BIASED NDIR GAS SENSING METHODOLOGY

CROSS REFERENCE TO RELATED APPLICATIONS

This application claims the benefit of 61/274,874, filed on Aug. 21, 2009, the disclosure of which is specifically incorporated herein by reference.

FIELD OF THE INVENTION

The present application is in the field of gas analysis, and specifically relates to apparatus using a Non-Dispersive Infrared (NDIR) gas analysis technique to determine the concentration of a particular type of gas present in a chamber by sensing the absorption of infrared radiation passing through the gas.

BACKGROUND OF THE INVENTION

Non-Dispersive Infrared (NDIR) gas sensors have been considered as one of the best methods for gas measurement since the 1950's. When compared to other gas detection methodologies such as electrochemical fuel cells, catalytic (platinum bead) sensors, photo-ionization detectors (PID), flame-ionization detectors (FID) etc., which are all referred to as "interactive" types of gas detectors, NDIR gas sensors are highly specific, sensitive, fast responding, relatively stable over time, rugged, reliable and easy to maintain.

Over six decades of incessant technology development for NDIR gas sensors began with the advent of the "Single Beam Methodology" exemplified by the Beckman LB-1 medical $CO_2$ sensor circa 1951-1955 which suffered from extremely poor output drift problems over temperature and time. The emergence of a variety of "Double Beam Methodology" took place during the period between the early 1960's and the mid-1970's, most notably represented by the development of Hewlett-Packard's Model 47210A Capnometer™, which was also a medical $CO_2$ sensor for monitoring the end-tidal $CO_2$ levels of cardiac and respiratory patients in the ICU's. (See Jaffe, MB "Infrared measurement of Carbon dioxide in the Human Breath: "Breathe-Through Devices from Tyndall to the Present Day" *Technology, Computing and Simulation* 2008; 107: 890-904.) In the Capnometer, a novel double beam technique known as "Negative Filtering" was advanced in the creation of a two-beam ratio signal processing scheme. This "Double Beam Methodology" was later improved by Burch et al. in U.S. Pat. No. 3,793,525 (1974) and by Blau Jr. in U.S. Pat. No. 3,811,776 (1974) in manners very similar to the "Negative Filtering" concept first introduced in the Hewlett-Packard's Capnometer.

As the fabrication technology for narrow band pass interference filters gradually advanced towards the end of the 1970's, gas cells that were used earlier for implementing NDIR Double Beam methodologies were quickly replaced by these filters. A simpler and less costly Double Beam methodology would involve a beam of infrared energy emanating from an infrared source and passing through a sample chamber containing an unknown amount of the gas whose concentration is to be determined. Before reaching an infrared detector, the beam is passed through two narrow band-pass filters which are mounted on a rotating wheel. One of the two filters passes only radiation at the characteristic absorption wavelength of the gas to be detected. The other filter will is used as reference filter at a wavelength close to, but not overlapping, that of the first filter. This type of NDIR gas analyzer implementing the Double Beam methodology requires the generation of some type of synchronizing signal in order to coordinate the operation of the signal processing circuit with the rotation of the filter wheel.

The period from the early 1980's to the early 1990's witnessed a rapid growth of diverse applications in the use of NDIR gas sensors. Besides the medical and HVAC industries which had been the mainstay for the need of NDIR gas sensors throughout the 1970's, other industries, such as mining, oil and gas production, diverse manufacturing, pharmaceutical etc., where safety and efficiency are invariably of the utmost importance, started to demand more and more NDIR gas sensors. Their demand did not focus just on the general availability in numbers and their detection of diverse gases, but also in the size, ruggedness and cost for these sensors. Throughout the 1970's NDIR gas sensors, especially those that implemented the Double Beam methodology of gas measurement, were bulky, relatively heavy and included moving parts such as mechanical light choppers. Beginning in the mid-1980's, researchers and developers of NDIR gas sensors concentrated on new sensor designs that were compact, lightweight and possessed no mechanical moving parts nor focusing optics. Such designs can be found in U.S. Pat. No. 5,026,992 entitled "Spectral Ratioing Technique for NDIR Gas Analysis Using a Differential Temperature Source" by Wong (Jun. 25, 1991), in U.S. Pat. No. 5,340,986 entitled "Diffusion-Type Gas Sample Chamber" by Wong (Aug. 23, 1994) and in U.S. Pat. No. 5,341,214 entitled "NDIR Gas Analysis Using Spectral Ratioing Technique" by Wong (Sep. 23, 1994).

One of the most noteworthy new designs for NDIR gas sensors was disclosed in U.S. Pat. No. 5,163,332 entitled "Gas Sample Chamber" by Wong (Nov. 17, 1992). A diffusion-type gas sample chamber for use in a gas sensor consists of an elongated hollow tube having an inwardly-facing specularly-reflective surface that permits the tube to function also as a light pipe for transmitting radiation from a source to a detector through the sample gas. A number of filtering apertures in the wall of the otherwise non-porous hollow tube permit the sample gas to enter and exit freely under ambient pressure. This invention for a simplified diffusion-type gas sample chamber provides a novel approach for reducing the complexity of NDIR gas measurement systems by eliminating the need for expensive optics, mechanical choppers and a pump for pulling or pushing the gas into the sample chamber. In addition, the sample chamber of this invention provides a long effective path length which increases the gas detection resolution and sensitivity.

From the mid-1990's onwards as the need and use of NDIR gas sensor for detecting all manners of gases in diverse industries continued to grow unabated, research and development efforts concentrated on new designs that would not only improve their performance characteristics, but also reduce the overall sensor cost with the use of multi-channel gas sensors. Many manufacturers took advantage of the so-called waveguide hollow tube sample chamber concept (see U.S. Pat. No. 5,163,332 cited above) and were able to introduce NDIR gas sensors that were significantly lower in unit price. New sensor designs that continued to take advantage of achievements discussed above can be found in U.S. Pat. No. 5,222,389 entitled "Multi-Channel Gas Sample Chamber" by Wong (Jun. 29, 1993) and in U.S. Pat. No. 5,502,308 entitled "Diffusion-Type Gas Sample Chamber" by Wong (Mar. 26, 1996).

In the first of these two disclosed new designs, several detectors equipped with different narrow band-pass interference filters as windows are mounted at the detector end of the so-called waveguide hollow tube sample chamber (see U.S. Pat. No. 5,163,332). By virtue of the fact that the waveguide sample chamber serves as a light pipe to conduct radiation via multiple reflections inside the highly reflective wall, the entire sample chamber is uniformly illuminated with radiation at a slowly decreasing intensity towards the detector end. Thus, at the detector end each of the several mounted detectors essentially receives the same radiation intensity from the common infrared source. Furthermore, each of the common source-detector pair has approximately the same path-length. Thus, if each of the several mounted detectors carries a different narrow band-pass filter that passes radiation which is absorbed by a particular gas present in the gas sample chamber, this new design essentially functions as a compact and low-cost multi-channel NDIR gas sensor.

In the second of the above disclosed new designs, a gas filter cell, inserted to the source/detector end of the waveguide sample chamber (see U.S. Pat. No. 5,341,214), is used to significantly reduce the influence of an interfering gas present in the sample chamber. Since the radiation source in this new design is mounted at the same end of the sample chamber as the detector, radiation emitted by the source is reflected from the other end of the sample chamber back to the detector after passing through the gas filter cell twice. The gas filter gas is filled with the interfering gas. In passing twice through the gas filter cell, the radiation generated by the source is greatly attenuated at wavelengths corresponding to the absorption bands of the interfering gas. Since interference occurs only at wavelengths where the absorption bands of the interfering gas overlap the absorption bands of the gas to be detected, the great attenuation of the radiation at such wavelengths by the gas filter cell substantially diminishes the extent of interference.

New NDIR gas sensor designs continued to be introduced well into the 2000's aimed further improving sensor performance and reducing unit production cost for NOIR gas sensors. In U.S. Pat. No. 7,259,374, entitled "Method for Detecting a Gas species Using a Super Tube Waveguide" by Wong (Aug. 21, 2007), the concept of using a hollow tube with an inwardly-facing specularly-reflecting surface as a functionally efficient sample chamber was extended from a one-dimensional straight tube to a multi-bend waveguide collectively greater than 180 degrees in three dimensions By so doing, the effective sample chamber path length of NDIR gas sensors can be elongated by more than an order of magnitude to 60' or longer. This new design can allow NDIR gas sensors to detect gas concentrations down to 1 ppm or less.

Another noteworthy new design for NDIR gas sensors was recently disclosed in U.S. Pat. No. 7,358,489 entitled "Ultra Low Cost NDIR Gas Sensors" by Wong (Apr. 15, 2008). In this new design, the concentration of a gas species is detected by using a single beam NDIR gas sensor in which an infrared source element is driven at two different temperatures. A feedback loop is designed to sense an operational voltage of the source. A differential gain amplifier is further designed to create a high cycle amplified output and a low cycle amplified output during respectively a high and low cycle pulsing of the source. Meanwhile a controller is used to synchronize the source driver so that a signal processor can determine the gas concentration through the use of the high and low cycle amplified outputs. This new methodology could further afford the use of a non-genuine blackbody source, such as an incandescent miniature light bulb, in order to minimize the unit production cost for this sensor.

Despite the over six decades of incessant technology development for NDIR gas sensors, there are still two important sensor performance deficiencies that have yet to be overcome. The first one is sensor output stability over time and the second one is sensor output inaccuracies due to other gases present with the gas to be measured because of interferences caused by the overlapping of their absorption bands. One of the most important sensor performance characteristics is indeed the sensor output stability over time without the need for periodic re-calibration. It is because of the fact that without an output stable $CO_2$ controller, for example, the implementation and practice of Demand Controlled Ventilation (DCV) strategy in office and commercial buildings to save energy would be very awkwardly inconvenienced. However, until the middle of the 1990's, no design was yet in sight to remedy this serious deficiency for NDIR gas sensors. It appeared that the only interim solution for solving this problem was through use of sensor output correction software. Such a sensor was disclosed in U.S. Pat. No. 5,347,474 (1994) entitled "Self-Calibration of an NDIR Gas Sensor" by Wong. This methodology is based upon the concept that some cyclic variables include within each cycle a value that can be extrinsically determined. In such a case, the sensed value may differ from the known value by an amount that is a combination of long-term drift of the sensor and random measuring error. The drift component can however be evaluated and eliminated by devising a specific method as follows. Once each cycle, for a number of cycles, the sensor measures the variable at a time when its value should equal the extrinsically-known value. The differences are plotted versus time, and a best-fitting straight line is determined, which indicates the drift. Throughout the next cycle as the variable is continuously sensed, the drift determined from the best-fitting straight line is continuously applied in small quantities in order to correct the sensed value.

Based upon the above discussion, it is clear that there has been a very long felt need that has remained unresolved, despite many decades of research and development, for creating NDIR gas sensors whose output is stable or substantially drifts free over time. The present invention solves this problem and sets forth an advance that will revolutionize the entire NDIR gas sensor industry.

SUMMARY OF THE INVENTION

The present invention is generally directed to an NDIR gas sensor and methodology in which an absorption bias between signal and reference outputs is used to determine sample concentration of a gas being measured. The absorption bias is created by using a signal channel with a path length that is greater than a path length of a reference channel in the sample chamber while both the signal and reference detectors have an identical narrow band pass filter with the same Center Wavelength ("CWL"), Full Width Half Maximum (FWHM) and transmittance efficiency at the CWL.

In a first, separate group of aspects of the present invention, the reference detector and the signal detector share a common thermal platform that can also be shared by the sample chamber and the infrared source.

It is therefore a primary object of the present invention to advance a new design for an NDIR gas sensor and methodology which, when appropriately implemented, renders the sensor output stable or substantially drift free over time.

This and further objects and advantages will be apparent to those skilled in the art in connection with the drawings and the detailed description of the invention set forth below.

DETAILED DESCRIPTION OF THE INVENTION

Before addressing the present invention, it will be worthwhile to review the conventional and ever so popular dual-beam methodology. For purposes of illustration, the dual-beam methodology that will be discussed is that for implementation of an NDIR $CO_2$ gas sensor.

Figure 1:
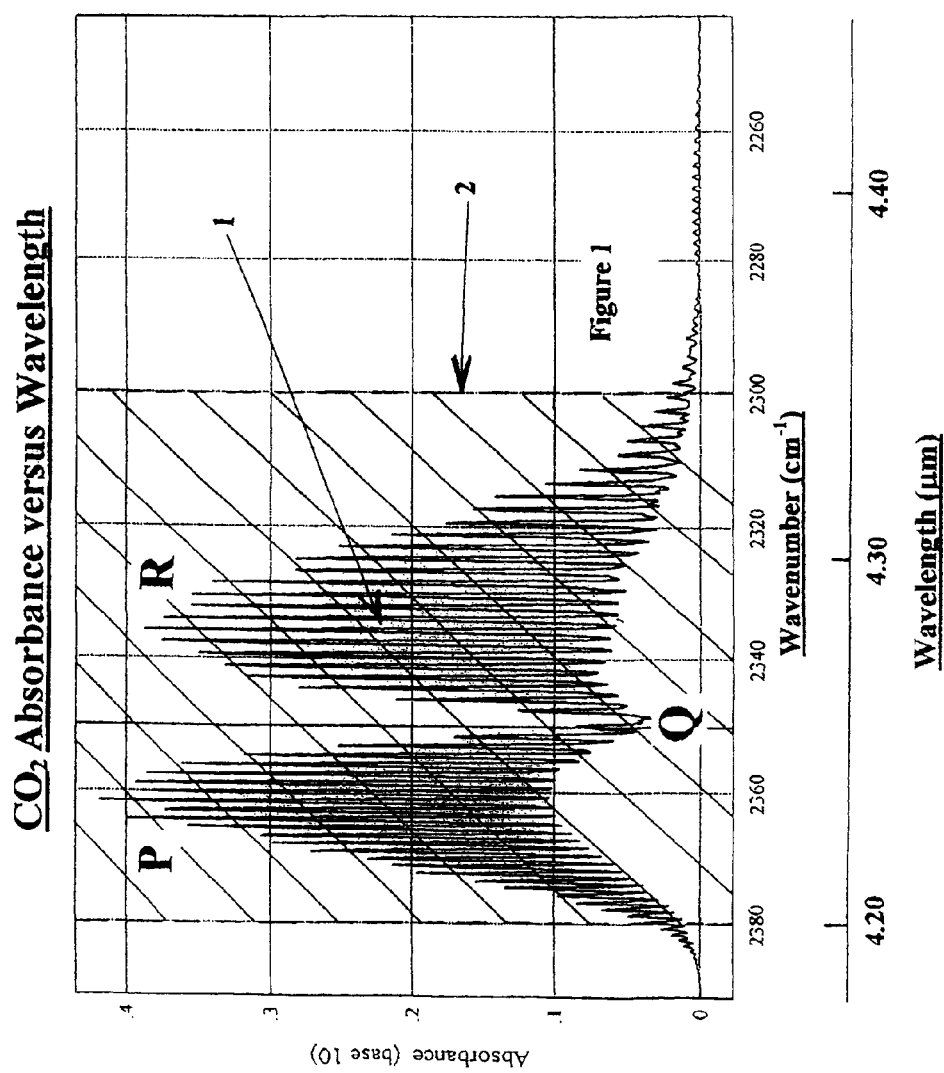
FIG. 1 depicts the 4.26μ infrared absorption bands of $CO_2$ expressed in absorbance units and a narrow band pass spectral filter with a Center Wavelength (CWT) at 4.26μ and a Full Width Half Maximum (FWHM) value of 0.14μ used optimally to detect this gas.

FIG. 1 shows the infrared absorption band 1 of $CO_2$ at 4.259μ showing, respectively, the P, Q and R branches. FIG. 1 also shows the spectral characteristics of a narrow band pass filter 2 with Center Wave Length CWL=4.26μ and a Full Width Half Maximum FWHM=0.14μ (shaded area) used in the design for the signal channel of a conventional NDIR $CO_2$ sensor. To complete this design, another spectral narrow band pass filter with CWL=3.91μ and FWHM=0.10μ, which does not overlap the 4.26μ absorption band of $CO_2$, is used for the reference channel. As can be seen from FIG. 1, the 4.26μ absorption band of $CO_2$ comprises a number of rotation-vibrational narrow absorption lines constituting the P and the R branches. The radiation emanating from the infrared source whose spectral positions (wavelengths) coincide with the narrow absorption lines of the P and R branches will be absorbed by the $CO_2$ gas as the radiation traverses the sample chamber containing same.

The technical foundation of NDIR gas sensors is based upon the law of absorption known as the Beer-Lambert Law, which is:

$$I/I_o = \exp(-kCL) \quad \text{Equation (1)}$$

where $I_o$=Initial radiation beam intensity
I=Beam intensity after traversing the gas to be detected
k=Absorption coefficient=AC/(0.434×C×L)
AC=Absorbance (Ordinate of FIG. 1)
C=Gas concentration
L=Sample path length defined typically by the effective sample chamber length of the sensor and
$I/I_o$=Transmission=1-Absorption=exp (−AC/0.434)

One can see from Equation (1) that the absorption of a beam of radiation traversing a sample of gas whose concentration level is to be determined is proportional to the absorption coefficient k of the gas in question, the gas concentration C and the path length L as defined by the sample chamber length for the sensor. Based upon the spectral characteristics of a typical infrared absorption band, see, e.g., FIG. 1 for $CO_2$ gas, the absorption of the intensity of a radiation beam by the gas could rarely be complete (i.e. 100% absorbed) unless the gas concentration approaches 100% and is also at a very high pressure (e.g. hundreds of bars) so that the individual narrow absorption lines of the branches coalesce together to form a bottomed-out spectral band.

Figure 2:
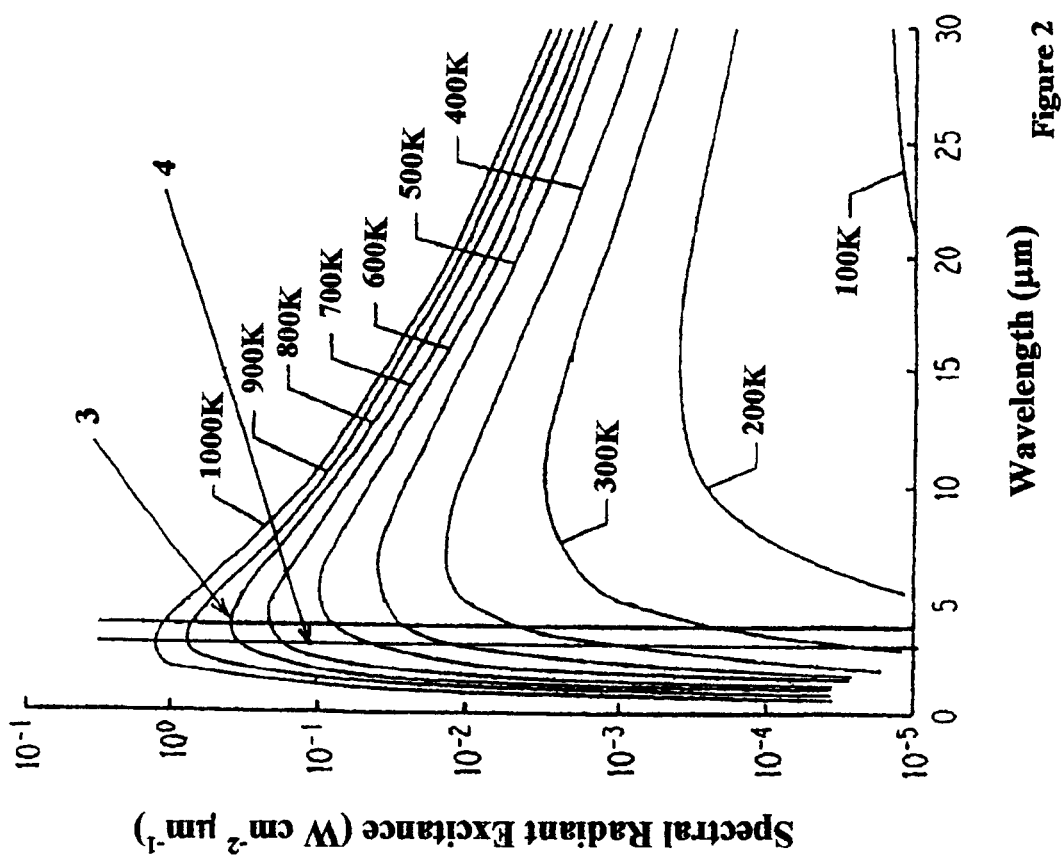
FIG. 2 depicts the conventional signal and reference narrow band pass filters at 4.26μ and 3.91μ, respectively, used in the design of a dual-beam NDIR $CO_2$ sensor superimposed on the spectral radiant excitance curves of a blackbody source at temperatures between 100° K and 1,000° K.

In the design for NDIR gas sensors, almost all infrared sources without exception are graybodies, so called because the emissivity of these sources is always less than unity. However, Planck's radiation law comprising a family of spectral radiation curves for sources of diverse temperatures represents equally well both graybody and blackbody (emissivity =1) sources. FIG. 2 depicts the spectral radiant excitance curves of a blackbody source at temperatures between 100° K and 1,000° K. Superimposed on this curve are the spectral locations for the signal, 3, and reference, 4, narrow band pass spectral filters at 4.26μ and 3.91μ, respectively.

By looking at FIG. 2 one can see that if the temperature of the source changes, thereby shifting the Planck's spectral radiation excitance curve, the relative magnitudes of the radiation traversing the two filters at their respective spectral locations will change and so will the ratio of their respective detector outputs. This is precisely the reason why the outputs of all NDIR gas sensors today that utilize this so-called "Double Beam" methodology will drift over time as the infrared source ages, resulting in a change of its spectral output intensities at the signal and reference filter wavelengths. Thus, the sensor output expressed as the ratio of the signal channel detector output over the same for the reference channel can never be held constant over time. Against the calibration curve for the sensor, the change of this ratio value is equivalent to a change or drift in the sensor output in the course of time.

Upon recognition of the foregoing, one can also recognize that using a spectral location where there is no infrared absorption by the gas of interest for establishing a reference channel cannot prevent the output of the so-designed NDIR gas sensor from drifting over time.

If one is to design an NDIR gas sensor whose output remains substantially drift-free over time, meaning that there is so little drift that any actual drift is insignificant and does not require a correction during use or the life of the sensor, one must make sure that there are no spectral content discrepancies delivered at any time to both the reference and the signal channels. Only in this way will the ratio of the signal detector output over the reference detector output remain substantially invariant even as the infrared source ages over time or as the temperature of the environ surrounding the sensor changes unpredictably over time.

The present invention achieves this revolutionary feat by applying the same spectral narrow band pass filter to both the signal and reference channels. An absorption bias is additionally applied to the signal channel by making the sample chamber path length associated with it longer than that associated with the reference channel.

Figure 3:
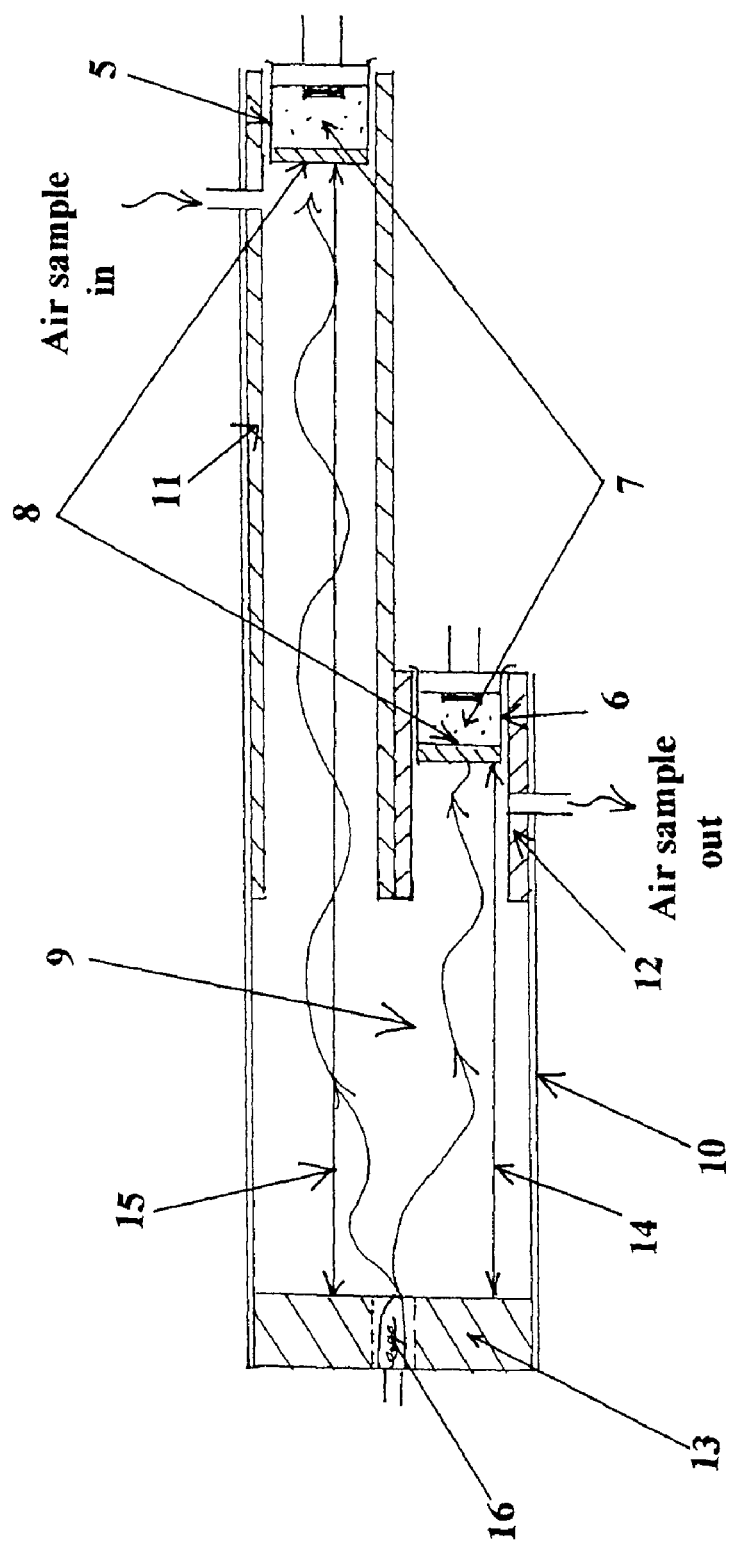
FIG. 3 depicts the schematic components layout for the Absorption Biased (AB) NDIR gas sensing methodology disclosed in the present invention.

FIG. 3 depicts conceptually the optical component layout for the present invention which is being named Absorption Biased methodology for NDIR gas sensors. As shown in FIG. 3, both the signal channel detector 5 and the reference detector channel 6 are entrapped with 100% Nitrogen 7 and have the same narrow band pass spectral filter 8 which is used to detect the gas of interest in the sample chamber 9. As an example, the filter designed to be used for the detection of $CO_2$ gas could have a Center Wavelength (CWT)=4.26μ and a Full Width Half Maximum (FWHM)=0.14μ. In an especially preferred embodiment of an NDIR gas sensor in accordance with the present invention both detectors 5 and 6 are thermally connected to the entire sensor body 10 through their respective waveguides 11 and 12 and consequently they always share the same thermal platform with each other. In other words, the entire sensor body 10, which is in essence a composite of aluminum parts comprising the infrared source mount 13, sample chamber 9 and the waveguides 11 and 12, respectively, for the signal and reference channels, provides an excellent common thermal platform for detectors 5 and 6. Because detectors 5 and 6 share the same common thermal platform, there should be no difference in temperature between the two detectors, or at least not any difference significant enough to interfere with their measurements over time since the thermal platform will equilibrate any localized temperature gradient over time.

As shown in FIG. 3, the sample chamber pathlength $L_R$, 14, associated with the reference channel is approximately one-half of the sample chamber pathlength $L_S$, 15, associated with the signal channel. Although this difference in pathlength is especially preferred, the difference in pathlength could be greater or less, as long as a detectable absorption bias is created so that the concentration of gas to be detected can be determined.

A common infrared source 16 is used to illuminate both the signal and the reference channels. The output of the detector 5 for the signal channel is always less than that of the detector 6 for the reference channel irrespective whether or not there is any amount of the gas of interest in the sample chamber 9. The respective detector outputs can be determined with the use of Equation (1) above for the particular gas of interest and the designed characteristics of the narrow band pass filter 8 together with the physical dimensions for $L_R$ 14 and $L_S$ 15.

Figure 4:
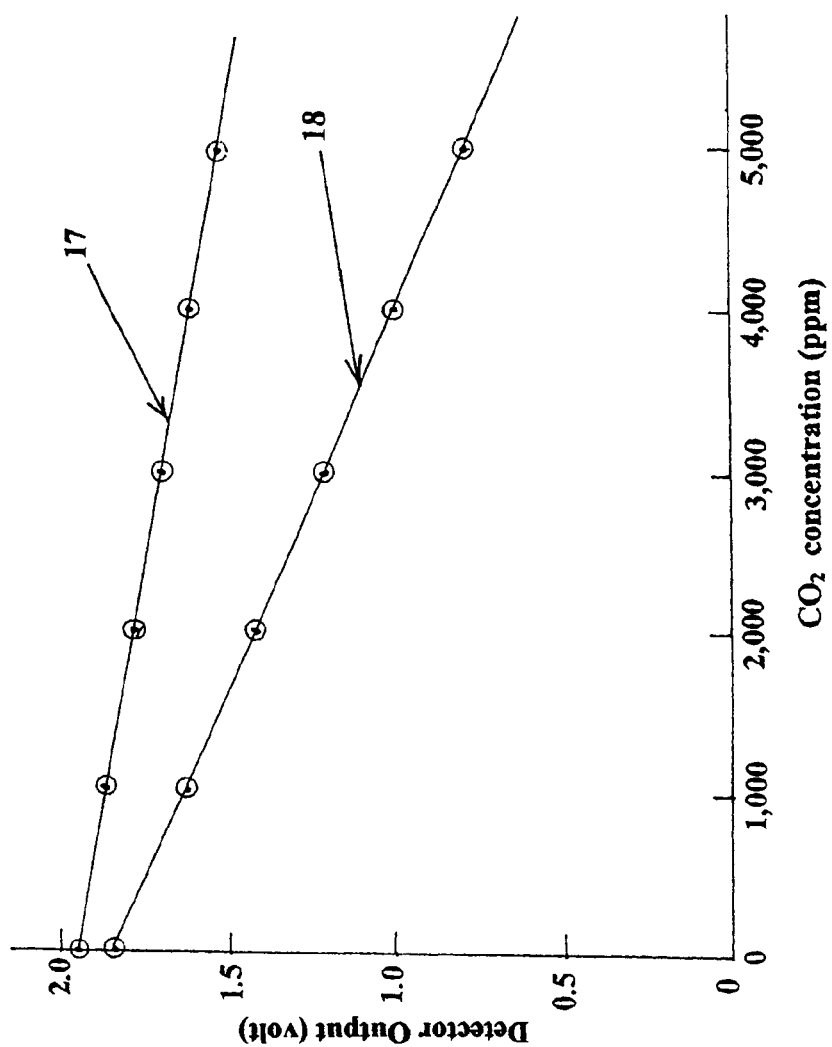
FIG. 4 depicts the detector outputs for the signal and reference channels as a function of $CO_2$ concentration in the sample chamber for the Absorption Biased (AB) NDIR gas sensing methodology.

FIG. 4 shows graph 17 depicting the output of the reference channel detector 6 as a function of $CO_2$ concentration in the sample chamber 9. Graph 18 of FIG. 4 shows the output of signal channel detector 5 as a function of $CO_2$ concentration in sample chamber 9. The detector output of signal channel detector 5 is less than that of reference channel detector because the sample pathlength $L_R$ of the reference channel is shorter than the signal channel sample pathlength $L_S$. Therefore, whenever $CO_2$ gas present in sample chamber 9, signal channel detector 5 will experience more absorption by the $CO_2$ gas than the corresponding reference channel detector due to its longer associated pathlength $L_S$.

Figure 5:
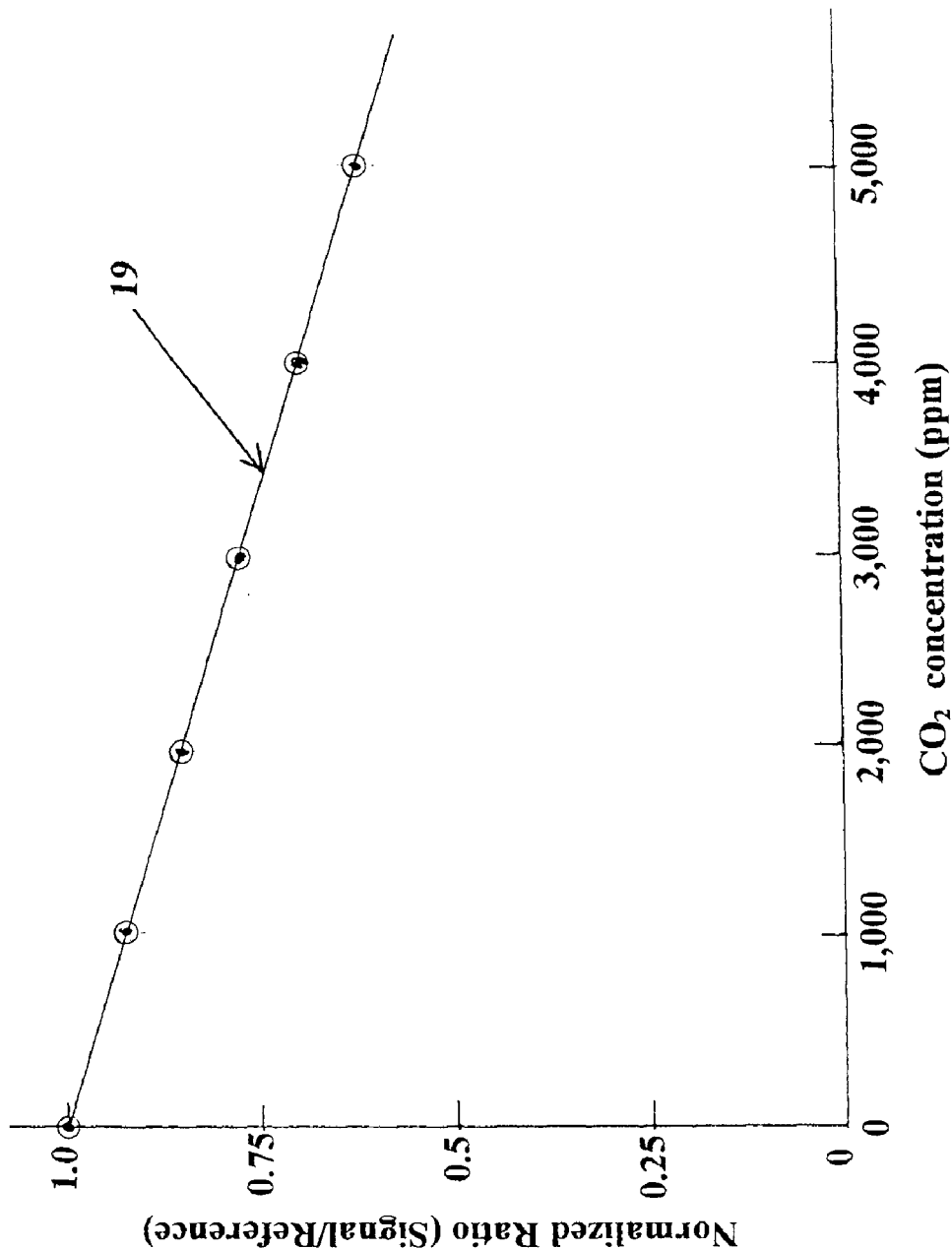
FIG. 5 depicts the normalized ratio of signal output/reference output as a function of $CO_2$ concentration in the sample chamber for the Absorption Biased (AB) NDIR gas sensing methodology.

FIG. 5 shows graph 19 depicting the values of the normalized ratio of the Signal channel detector output over the Reference channel detector output. The ratio is normalized to the value when there is no $CO_2$ gas present in the sample chamber 9. The normalized ratio always starts out at a value of unity when there is zero $CO_2$ concentration in the sample chamber 9 as shown by graph 19 in FIG. 5. Graph 19 is, in essence, the calibration curve for the sensor implemented with the presently invented Absorption Biased (AB) methodology. For $CO_2$ detection, both the signal and the reference channels utilize exactly the same narrow band pass spectral filter characterized by having CWL=$4.26\mu$ and FWHM=$0.14\mu$ for spectral radiation selection. It is especially preferred that the detectors for both channels, including their filters, are mounted on the same thermal platform (see FIG. 3) and always have about the same temperature. The value of the ratio (Signal/Reference) is henceforth rendered independent of the spectral changes for the source over time (aging) and also independent of the temperature changes in the environ surrounding the sensor at any given time.

Although the current Absorption Biased methodology for designing NDIR gas sensors has been described by way of illustration only with a dual-beam $CO_2$ gas sensor, the methodology itself is applicable to any gas having a distinct infrared absorption band. Similar substantially drift free NDIR gas sensors can also be readily designed for water vapor ($H_2O$) utilizing its $2.70\mu$ absorption band, Hydrocarbon (HC) at $3.46\mu$, Methane ($CH_4$) at $3.40\mu$, Carbon Monoxide (CO) at $4.65\mu$, Nitrous Oxide ($N_2O$) at $4.40\mu$ and so on, to name just a few. Accordingly, the present invention is applicable to NDIR gas sensors for use in detecting any chosen gas and should revolutionize the entire NDIR gas sensor industry because it now provides a way to obtain economical NDIR gas sensors, for all types of uses, that are substantially drift free.

While the invention has been described herein with reference to certain examples, those examples have been presented for illustration and explanation only, and not to limit the scope of the invention. Additional modifications and examples thereof will be obvious to those skilled in the art having the benefit of this detailed description. Further modifications are also possible in alternative embodiments without departing from the inventive concept.

Accordingly, it will be apparent to those skilled in the art that still further changes and modifications in the actual concepts described herein can readily be made without departing from the spirit and scope of the disclosed inventions as defined by the following claims.

What is claimed is:

1. A Non-Dispersive Infrared ("NDIR") gas sensor for detecting the presence of a chosen gas, comprising:
   a single infrared source for generating infrared radiation into a sample chamber to illuminate a signal channel path length and a reference channel path length;
   a signal detector located in the signal channel path length;
   a reference detector located in the reference channel path length; and
   electronics for determining a sample concentration of the chosen gas;
   wherein each of the reference detector and the signal detector have an identical narrow band pass filter with the same Center Wavelength ("CWL"), Full Width Half Maximum (FWHM) and transmittance efficiency at the CWL;
   wherein the electronics is calibrated by use of a calibration curve generated by using a normalized ratio of signal to reference outputs that starts at unity when there is zero concentration of the chosen gas;
   wherein the calibrated electronics determines a sample concentration of the chosen gas in the sample chamber by use of an absorption bias between a signal output of the signal detector and reference output of the reference detector obtained solely from use of the single infrared source; and
   wherein the single infrared source is the only source of infrared radiation emitted into the sample chamber.

2. The NDIR gas sensor of claim 1 wherein the signal channel path length is comprised of a signal channel waveguide and the reference channel path length is comprised of a reference channel waveguide.

3. The NDIR gas sensor of claim 2 wherein the signal channel waveguide does not contain a light path within the reference channel waveguide.

4. The NDIR gas sensor of claim 3 wherein the signal channel waveguide is parallel to the reference channel waveguide.

5. A process for determining a sample concentration of a chosen gas in a sample chamber of a Non-Dispersive Infrared ("NDIR") gas sensor, comprising:
   using a calibration curve generated by using a normalized ratio of a signal output detected by a signal detector to a reference outputs detected by a reference detector, wherein the normalized ratio starts at unity when there is zero concentration of the chosen gas to calibrate electronics used in the NDIR gas sensor;

emitting infrared radiation from a single infrared source into a sample chamber having both a signal channel path length and a reference channel path length, the signal channel path length being longer than the reference channel path length; and using the calibrated electronics to determine the sample concentration by use of an absorption bias created between the signal output and the reference output due to the difference in lengths between the signal channel path length and the reference channel path length, said determination being made by using the reference output and the signal output obtained solely from use of the single infrared source;

wherein the signal detector and the reference detector have an identical narrow band pass filter with the same Center Wavelength ("CWL"), Full Width Half Maximum (FWHM) and transmittance efficiency at the CWL, the signal detector detecting the chosen gas in a signal channel of the sample chamber with a signal path length that is greater than a reference path length of a reference channel in the sample chamber.

6. The NDIR gas sensor of claim 5 wherein the signal channel path length is comprised of a signal channel waveguide and the reference channel path length is comprised of a reference channel waveguide.

7. The NDIR gas sensor of claim 6 wherein the signal channel waveguide does not contain a light path within the reference channel waveguide.

8. The NDIR gas sensor of claim 7 wherein the signal channel waveguide is parallel to the reference channel waveguide.

* * * * *